Figure 1:
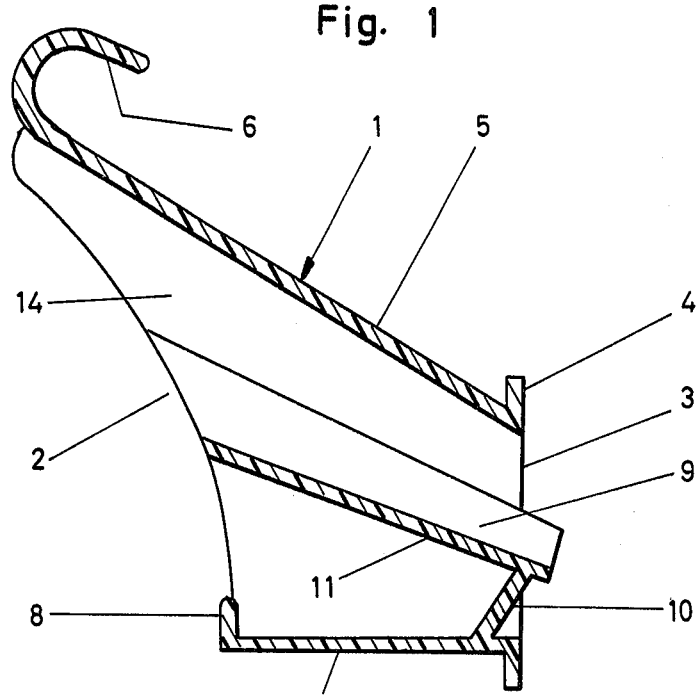

United States Patent [19]

Heimreid

[11] 4,304,013
[45] Dec. 8, 1981

[54] URINATION DEVICE FOR BEDRIDDEN FEMALE PATIENTS

[75] Inventor: Ken Heimreid, Heistad, Norway

[73] Assignee: Bryns Patentkontor, Oslo, Norway

[21] Appl. No.: 98,116

[22] Filed: Nov. 27, 1979

[30] Foreign Application Priority Data

Jul. 8, 1979 [NO] Norway ................................. 792263

[51] Int. Cl.³ ............................................ A47K 11/02
[52] U.S. Cl. ..................................... 4/144.3; 128/761; D24/54
[58] Field of Search ............................ 4/144.1–144.4, 4/113.1, 114.1, 301; 128/295, 761–763; D24/54; 141/297, 331

[56] References Cited

U.S. PATENT DOCUMENTS

| | | | |
|---|---|---|---|
| 587,803 | 8/1897 | Ewer | 4/144.1 |
| 2,628,617 | 2/1953 | Wright | D24/54 X |
| 2,941,532 | 6/1960 | Borin | D24/54 X |
| 3,072,125 | 1/1963 | O'Brien | D24/54 X |
| 3,161,891 | 12/1964 | Bauman | D24/54 X |
| 3,499,327 | 3/1970 | Lane, Jr. | 4/144.1 X |
| 3,815,581 | 6/1974 | Levin | 4/144.3 X |
| 3,929,412 | 12/1975 | Villari | 4/144.1 X |
| 3,995,329 | 12/1976 | Williams | 128/295 X |
| 4,020,843 | 5/1977 | Kanall | 4/144.3 X |
| 4,040,791 | 8/1977 | Kuntz | 128/295 X |

Primary Examiner—Stuart S. Levy
Attorney, Agent, or Firm—Cushman, Darby & Cushman

[57] ABSTRACT

A urination device for bedridden female patients, in the form of a funnel-shaped device adapted to be placed against and at least partially around the vulva.

4 Claims, 3 Drawing Figures

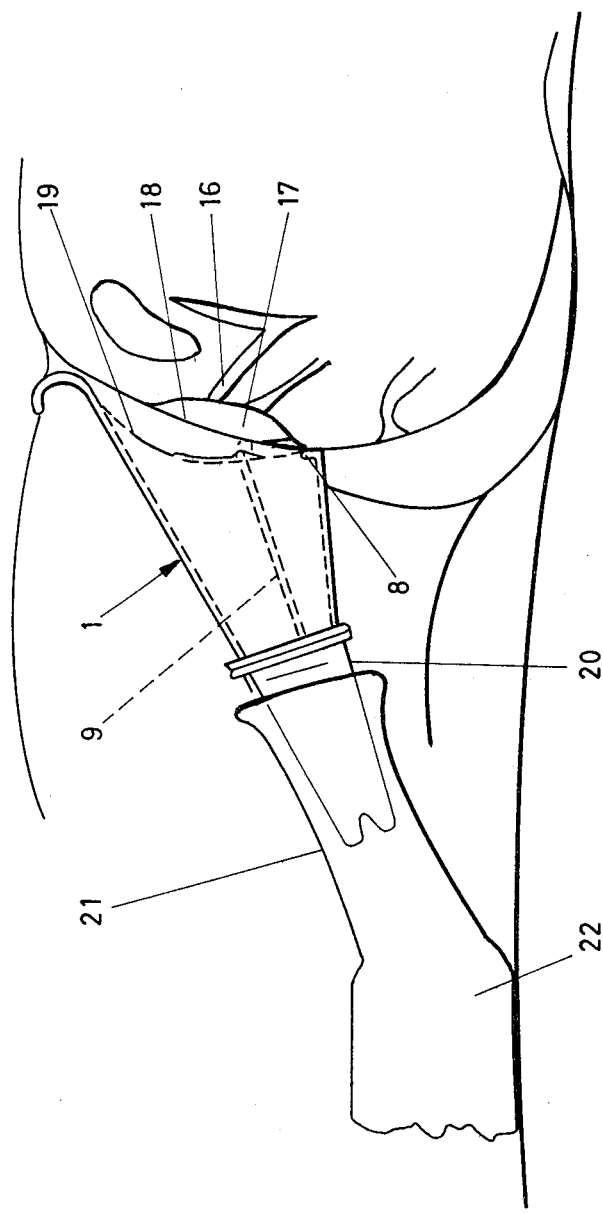

URINATION DEVICE FOR BEDRIDDEN FEMALE PATIENTS

The invention relates to a urination device for bedridden female patients. Bedridden women have to resort to the use of various types of bedpans. The use of a bedpan has several obvious drawbacks. It is uncomfortable for the user, because it is impossible to prevent urine from running backwards and downwards into the cleft between the buttocks. This occurs even if one tries as hard as possible to sit at least half-way upright during urination. The spreading of urine to the vaginal orifice and further backwards is naturally undesirable, especially for hygienic reasons. The placement of the bedpan also frequently requires the assistance of a nurse or other aide. The use of bedpans, for example, in a hospital, entails a great deal of work, because the bedpans have to be emptied, washed and sterilized. In the case of a metal bedpan, the weight of the pans, especially a stack of bedpans, is another minus factor.

The purpose of the invention, therefore, is to provide a urination aid for women with which one avoids the above difficulties and which facilitates urination to a substantial degree, also from the psychological point of view. According to the invention, therefore, a urination device for bedridden female patients is provided, said device being characterized by a funnel-shaped contrivance which is adapted to be placed against and at least partially around the vulva.

The funnel can well be connected to a conventional urine bottle used for male patients, or it can be connected to a drainage tube which empties into a collector vessel outside the bed. In use, the funnel is pressed against the vulva, and the soft folds of skin which form the labia will be pressed together and adapt themselves to seal tightly around the inlet edge of the funnel. Not only does one eliminate the above-mentioned drawbacks, but one also obtains several distinct advantages with the new urination device. The funnel can be manufactured inexpensively, preferably of a suitable plastics material, and can in fact be considered a disposable item. The funnel can naturally also be utilized repeatedly by one and the same patient, and it can be applied over an extended period of time without much discomfort for the patient. For example, for patients suffering from paralysis, the funnel-shaped device can be incorporated in an abdominal belt, a panty-like device, etc.

When the device is used on incontinent patients, one can more easily take urine specimens without the risk of feces contaminating the specimen. For incontinent patients, catheters are utilized for urination and for taking urine specimens, and the use of the new device in such cases can contribute to reducing the use of catheterization, thus also reducing the associated risk of infection.

As mentioned above, the funnel is adapted to be placed against and partially to surround the vulva. It will often be advantageous if the active funnel inlet cross section can be made narrower, and according to the invention this is done by providing a partition inside the funnel, running in the longitudinal direction of the funnel. This partition will then form a trough for the urine and thus reduce the risk of urine spillage even further. The edge of the partition lying in the inlet opening will press against the vulva during the use of the urination device, i.e., pressing against both the labia majora and labia minora, thus providing a restricted, outwardly-sealed area around the mouth of the urethra.

The funnel-shaped device can with advantage be connected to a sleeve, preferably conical in shape, and adapted to fit in the neck of a urine bottle or bag, but the funnel can also be made as a unit comprising such a sleeve, or it can be formed in some other suitable way at the outlet side to permit its connection to a desired collector vessel or drain.

Said internal partition, which forms a trough for the urine, preferably extends a short distance outside the outlet opening of the funnel. This is especially advantageous if provided in connection with an overflow wall at the outlet opening of the funnel, beneath the internal partition. This overflow wall will prevent urine from flowing back into the bottom region of the funnel. When reference is made above and in the following to an upper portion, lower portion, bottom region, etc., these terms refer to the normal position of the funnel during use, i.e., with the longitudinal direction of the funnel running approximately horizontally or diagonally downwards.

In one practical embodiment, the partition is V-shaped in cross section, and the overflow wall is formed by a transverse wall in the outlet opening, extending up to the bottom of the V. Between the V and the overflow wall edge, therefore, two openings will be formed such that there will be an open connection above the overflow wall. Thus, the overflow wall not only prevents urine from flowing backwards, but it also permits any urine which might have collected beneath the trough and inside the bottom region of the funnel to be able to flow past the overflow wall as soon as enough urine has collected.

The partition wall, or the shape of the trough, is not critical. For example, one might use a reversed V-shape. The overflow wall would then preferably be formed by a transverse wall in the outlet opening, extending up to the transition between the partition and the walls of the funnel, such that one also in this case would obtain an opening between the upper limit of the overflow wall and the underside of the trough.

A lower, low marginal wall can also advantageously be arranged at the inlet to the funnel. When the urination device is in use, this low marginal wall will also press against the vulva or the adjacent areas in back of the vulva and effect a seal. At the same time, the low marginal wall presents any urine which might come into the lower bottom region of the funnel from flowing back and possibly flowing out between the buttocks.

In a practical embodiment of the funnel-shaped device, a portion of the funnel's upper wall at the inlet opening can be extended and curved backwards in the direction of the outlet opening, thus forming a hook for hanging up the funnel and a handle to aid one in correctly and securely positioning the funnel during use. With this hook, the funnel can be suspended, for example, in a suitable stand beside the bed, or on a suitable stand for washing and disinfecting, if one wishes to utilize the new urination device not only as a disposable item, but as a more permanent product for repeated usage.

Figure 2:
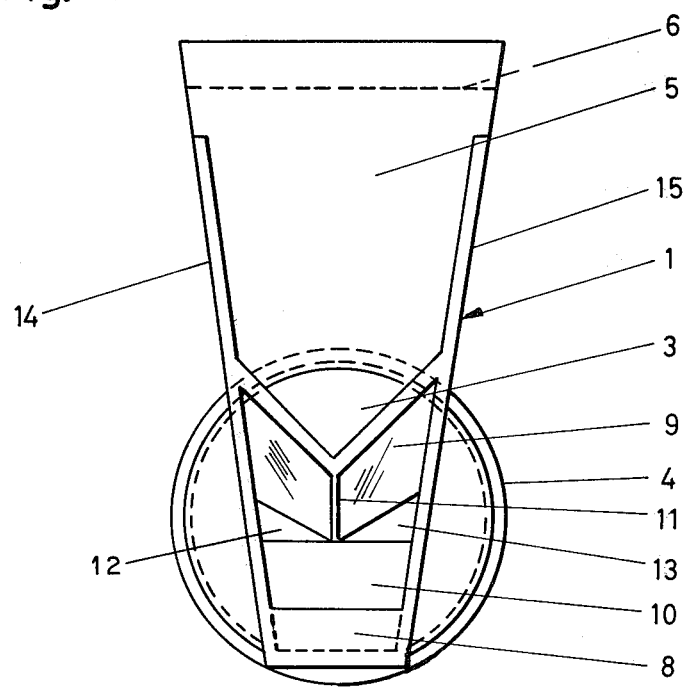

The invention will be elucidated in more detail in the following with reference to the accompanying drawings, where FIG. 1 shows a longitudinal cross section through the urination device of the invention, FIG. 2 shows the device of FIG. 1 from the inlet side, and FIG. 3 is a schematic cross section showing the urination device correctly positioned on a patient.

As can be seen on FIGS. 1 and 2, the new urination device is shaped as a funnel. The cross section of the funnel can be rectangular, oval or of some other suitable shape, for example, trapezoidal, as shown in FIG. 2. In FIGS. 1 and 2, the funnel is shown in approximately full scale.

The funnel 1 is manufactured of a suitable plastics material, utilizing known molding techniques. The funnel 1 has a trapezoidal cross section at the inlet opening 2 and tapers to a circular cross section 3 at the outlet opening. Around the outlet opening 3, a flange 4 is indicated for connecting the funnel to, for example, a sleeve extension, as shown in FIG. 3. The upper wall 5 of the funnel is extended at the inlet opening and curved backwards to form a hook 6. The bottom wall 7 of the funnel, at the inlet opening 2, is provided with a low marginal wall 8.

Inside the funnel, a partition wall 9 is provided in the longitudinal direction of the funnel, forming a trough for the urine. This partition or trough extends from the inlet opening 2 and back toward the outlet opening, and in this case extends a distance beyond the outlet opening. Beneath the V-shaped trough 9, at the outlet opening, an overflow wall 10 is provided which extends up to the outer bottom edge 11 of the V. On both sides of this bottom edge 11, therefore, free openings 12 and 13 will be found above the overflow wall 10.

The substantially vertical side walls 14 and 15, as shown in the vertical section in FIG. 1, have been given a curved configuration adapted to the shape of the human body.

In FIG. 3, the urination device is shown in place on the human body. This drawing is purely schematic, and does not show the compression of the vulva, but one will understand that when the funnel 1 is pressed against the vulva, the soft labia will conform to its shape, sealing against and partially around the inlet opening of the funnel. In FIG. 3, the urethra is designated 16, the vaginal area 17, and the inner and outer labia as 18 and 19, respectively. The urination device 1 has in FIG. 3 been extended by a conical sleeve 20 which fits into the neck 21 of a urine bottle 22. Instead of the arrangement illustrated here, the funnel could be made integral with the sleeve 20, or be formed to include a normal drainage hose which would lead to a desited waste outlet or collecting location.

FIG. 3 suggests the manner in which the partition or trough 9 will press against the vulva, and one can also see how the lower, rearward marginal wall 8 will be pressed against the body, such that the labia may possibly lie above the upper edge of the marginal wall 8.

The invention is naturally not restricted to the embodiment example shown and described herein. As mentioned previously, the cross-sectional configuration of the funnel is not critical, but one should aim at obtaining a cross-sectional configuration, especially at the inlet opening, which is adapted to the shape of the female organs.

Having described my invention, I claim:

1. A urination device for bedridden female patients comprising a funnel-shaped device the larger end of which is adapted to be placed against and at least partially around the vulva, said device having an inlet opening at its larger end and an outlet opening at the opposite end, an internal partition extending in the longitudinal direction of the device and projecting out beyond said outlet opening, said partition forming a trough for urine, an overflow wall at said outlet opening beneath said internal partition, and a bottom wall having at said inlet opening a low marginal wall adapted to be pressed against the body of the patient.

2. A urination device as in claim 1 wherein the funnel-shaped device is connected to a sleeve which is adapted for insertion into the neck of a urine bottle or bag.

3. A urination device as in claim 1 wherein the internal partition is V-shaped in cross section, and wherein the overflow wall is formed by a transverse wall in the outlet opening, extending up to the bottom of the V.

4. A urination device as in claim 1 wherein a part of the upper wall of the funnel at the inlet opening is extended and curved backwards toward the outlet opening, thereby forming a hook which can be used to suspend the device or as a handle.

* * * * *